(12) United States Patent
Malinowski

(10) Patent No.: US 10,758,734 B2
(45) Date of Patent: Sep. 1, 2020

(54) IMPLANTABLE MEDICAL DEVICE WITH A SILICONE HOUSING

(71) Applicant: Boston Scientific Neuromodulation Corporation, Valencia, CA (US)

(72) Inventor: Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 188 days.

(21) Appl. No.: 15/889,794

(22) Filed: Feb. 6, 2018

(65) Prior Publication Data

US 2018/0243569 A1 Aug. 30, 2018

Related U.S. Application Data

(60) Provisional application No. 62/464,865, filed on Feb. 28, 2017.

(51) Int. Cl.
*A61N 1/00* (2006.01)
*A61N 1/375* (2006.01)
*A61N 1/08* (2006.01)
*A61N 1/36* (2006.01)

(52) U.S. Cl.
CPC ............. *A61N 1/3752* (2013.01); *A61N 1/08* (2013.01); *A61N 1/36* (2013.01); *A61N 1/375* (2013.01)

(58) Field of Classification Search
CPC .......... A61N 1/3752; A61N 1/08; A61N 1/36; A61N 1/375
See application file for complete search history.

(56) References Cited

U.S. PATENT DOCUMENTS

| | | | |
|---|---|---|---|
| 6,516,227 B1 | 2/2003 | Meadows et al. | |
| 6,572,878 B1 | 6/2003 | Blaine | |
| 7,742,817 B2 | 6/2010 | Malinowski et al. | |
| 7,761,165 B1 * | 7/2010 | He ................. | A61N 1/0551 607/36 |
| 8,335,569 B2 | 12/2012 | Aghassian | |
| 8,498,716 B2 | 7/2013 | Chen et al. | |
| 8,626,309 B1 | 1/2014 | Alshemari | |
| 8,768,453 B2 | 7/2014 | Parramon et al. | |

(Continued)

OTHER PUBLICATIONS

U.S. Appl. No. 62/464,710, filed Feb. 28, 2017, Malinowski.

(Continued)

*Primary Examiner* — Scott M. Getzow
(74) *Attorney, Agent, or Firm* — Lewis & Reese, PLLC

(57) ABSTRACT

An implantable medical device (IMD) includes a housing that is formed of a biocompatible material such as silicone. The housing includes integral contact receptacles that house individual contacts, which contacts are electrically connected to electrical circuitry within a main interior cavity of the housing. The integral contact receptacles receive electrode leads, and the contacts are aligned with electrode terminals on the proximal end of the electrode leads, which establishes an electrical connection between the electrical circuitry and electrodes at the distal end of the leads. The housing is filled with a silicone gel such as a tacky diphenyl silicone gel. The silicone gel provides electrical, mechanical, and thermal insulation, and prevents the ingress of bodily fluids when the IMD is implanted.

19 Claims, 9 Drawing Sheets

(56) References Cited

U.S. PATENT DOCUMENTS

| | | | |
|---|---|---|---|
| 8,874,206 B2* | 10/2014 | Malinowski | A61N 1/36 |
| | | | 607/2 |
| 9,084,380 B2 | 7/2015 | Malinowski et al. | |
| 2002/0147488 A1 | 10/2002 | Doan et al. | |
| 2004/0068313 A1 | 4/2004 | Jenney et al. | |
| 2004/0186542 A1 | 9/2004 | Van Venrooij et al. | |
| 2005/0282977 A1 | 12/2005 | Stempel et al. | |
| 2009/0048580 A1* | 2/2009 | Gibson | A61F 11/00 |
| | | | 604/514 |
| 2010/0063555 A1* | 3/2010 | Janzig | A61N 1/3752 |
| | | | 607/2 |
| 2011/0046729 A1* | 2/2011 | Schuessler | A61F 2/12 |
| | | | 623/8 |
| 2011/0054563 A1 | 3/2011 | Janzig et al. | |
| 2011/0301670 A1 | 12/2011 | Gross et al. | |
| 2012/0095529 A1 | 4/2012 | Parramon et al. | |
| 2012/0109036 A1 | 5/2012 | Sambasivam et al. | |
| 2012/0221074 A1* | 8/2012 | Funderburk | A61N 1/3752 |
| | | | 607/45 |
| 2012/0259381 A1* | 10/2012 | Smith | H01R 13/5224 |
| | | | 607/46 |
| 2014/0277260 A1 | 9/2014 | Khalil et al. | |
| 2014/0295688 A1* | 10/2014 | Deininger | A61N 1/3752 |
| | | | 439/271 |
| 2015/0080982 A1 | 3/2015 | Funderburk | |
| 2017/0050023 A1 | 2/2017 | Hillbratt et al. | |

OTHER PUBLICATIONS

NuSil Technology GEL-8250 Product Profile, May 20, 2014, 3 pages.

NuSil Technology MED-6345 Product Profile, Apr. 5, 2007, 2 pages.

Velderrain, Michelle, "Designing Low Permeability, Optical-Grade Silicone Systems—Guidelines for Choosing a Silicone Based on Transmission Rates for Barrier Applications," NuSil Technology, 2012, 8 pages.

International Search Report and Written Opinion regarding corresponding PCT Application No. PCT/US2018/017286, dated May 24, 2018.

* cited by examiner

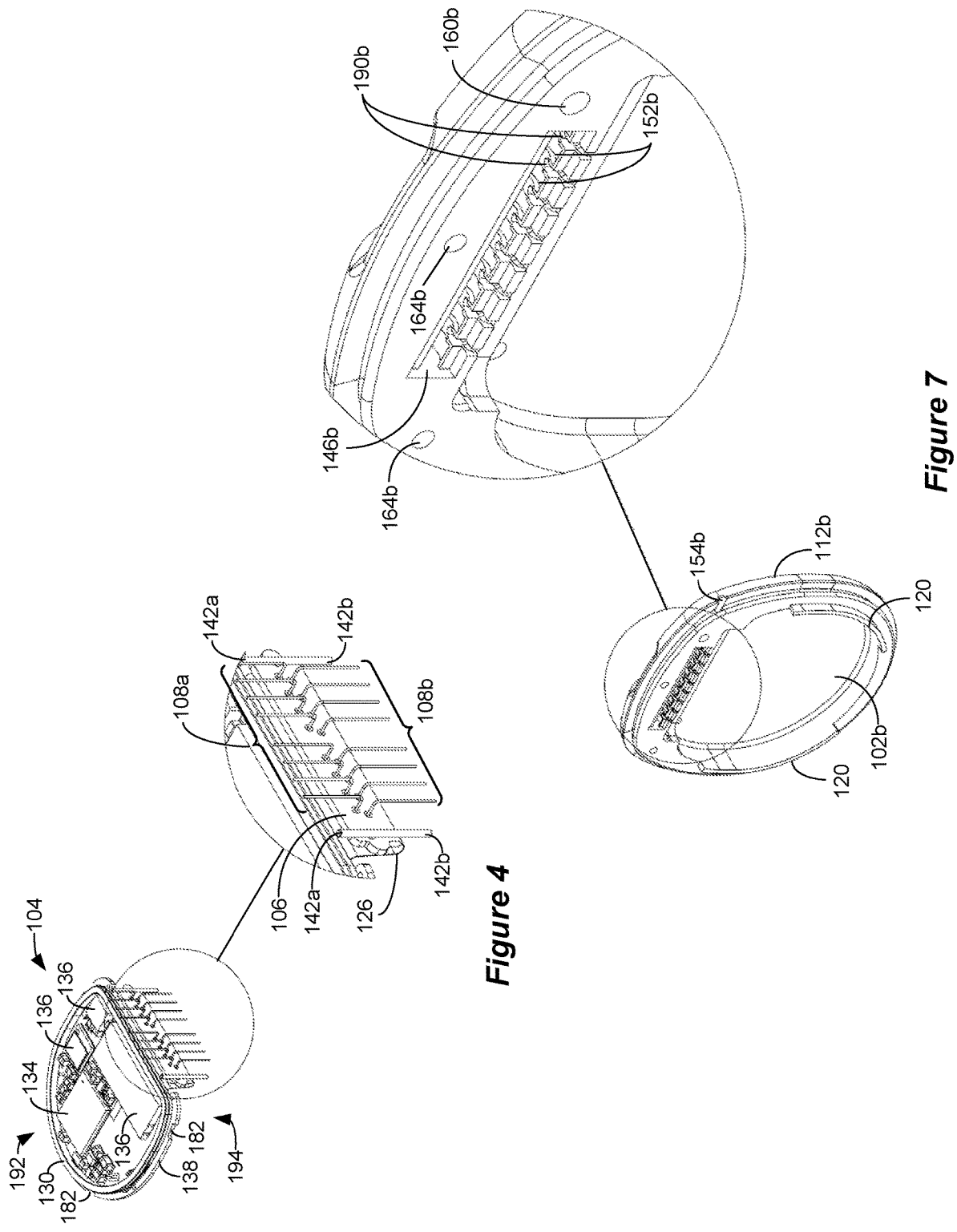

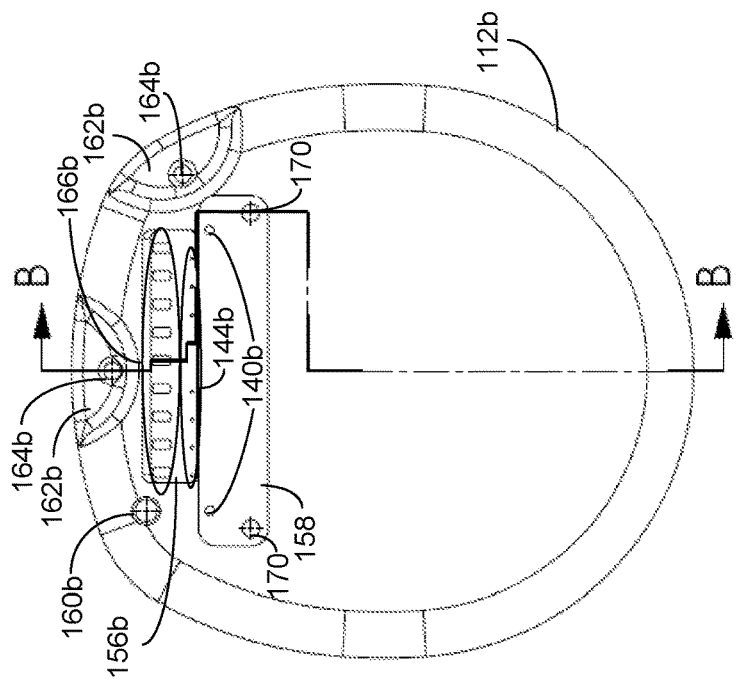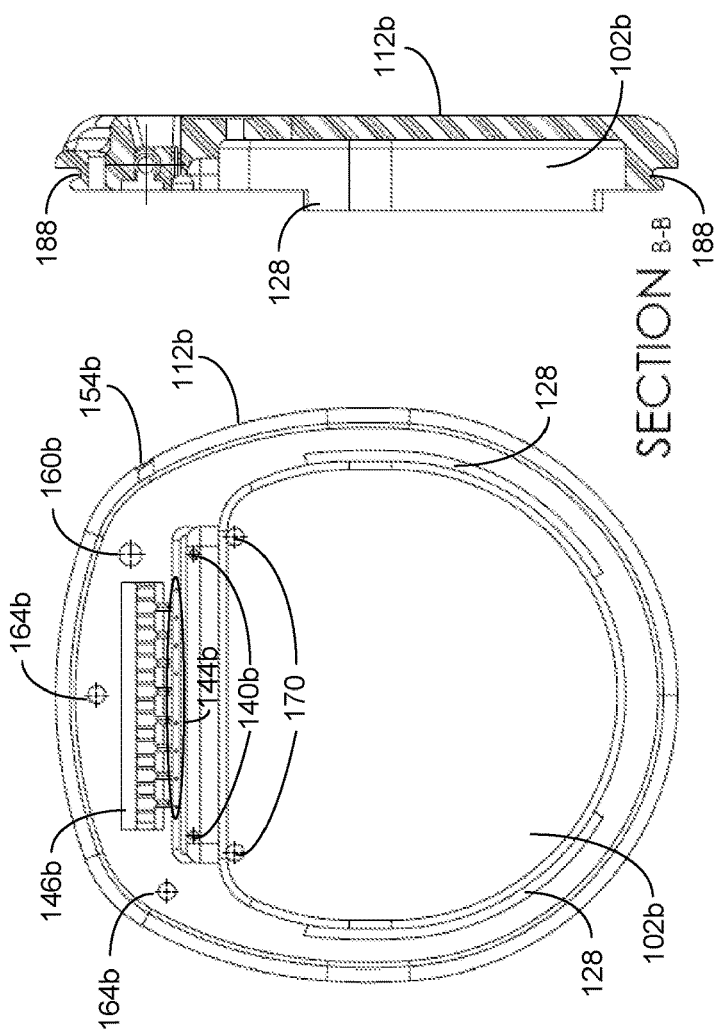

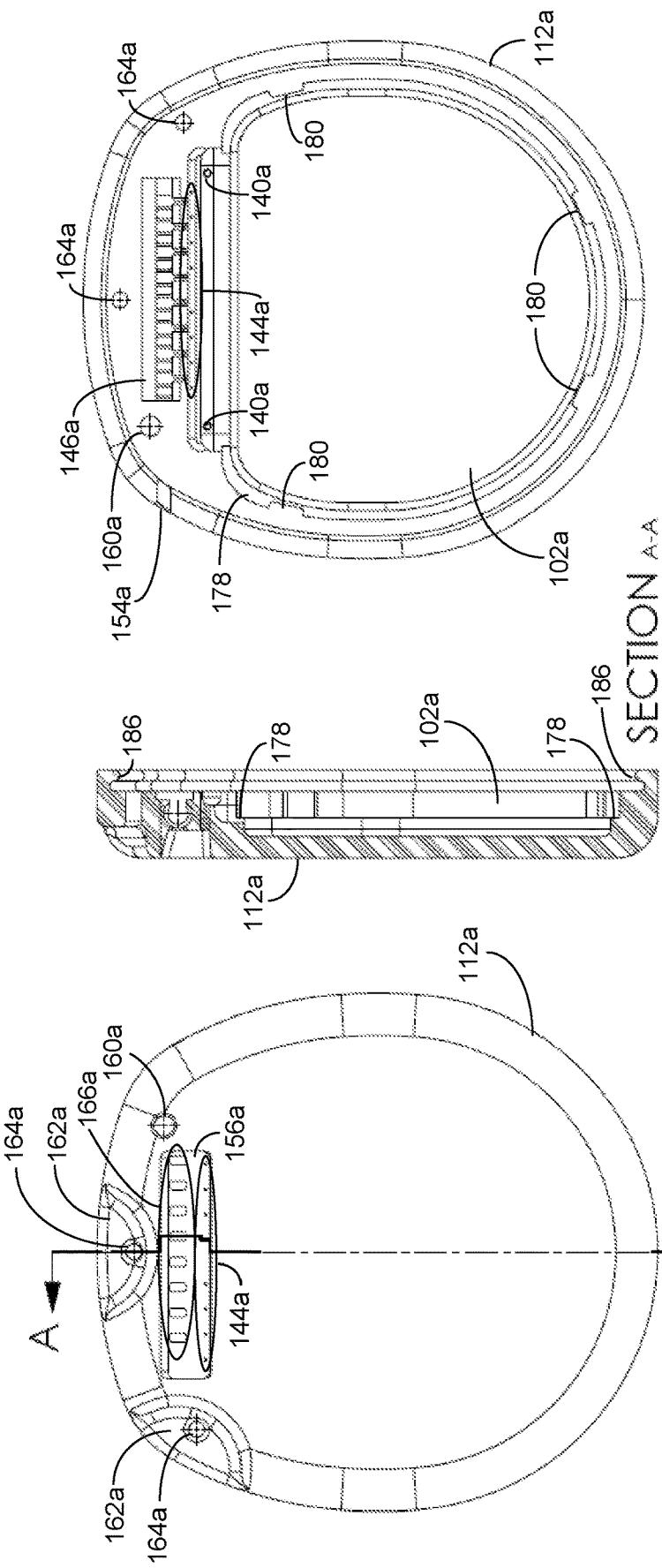

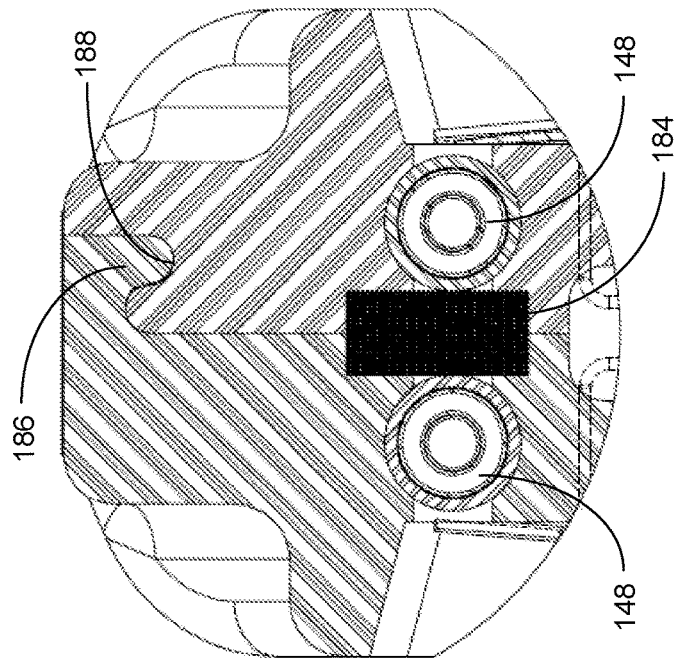
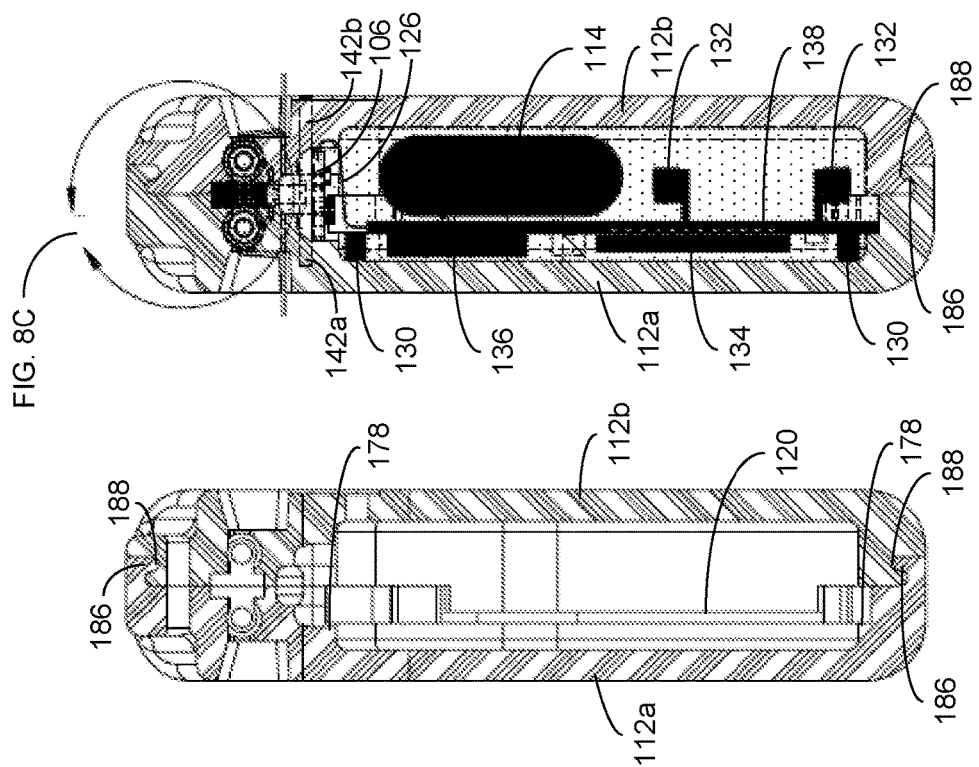

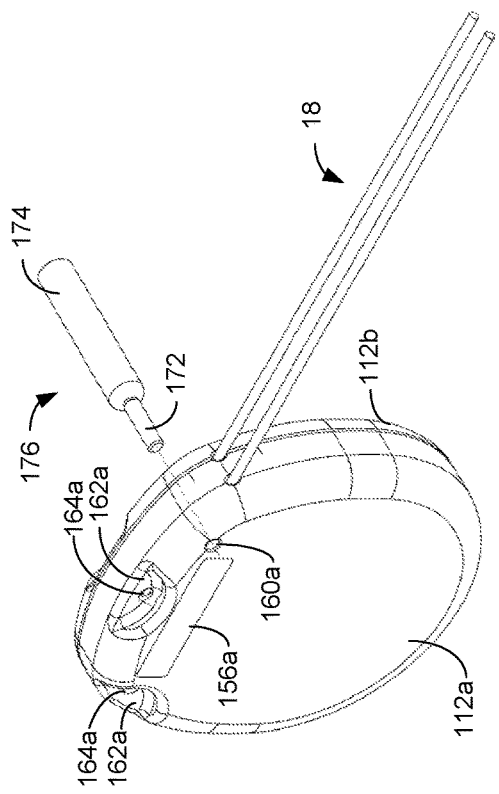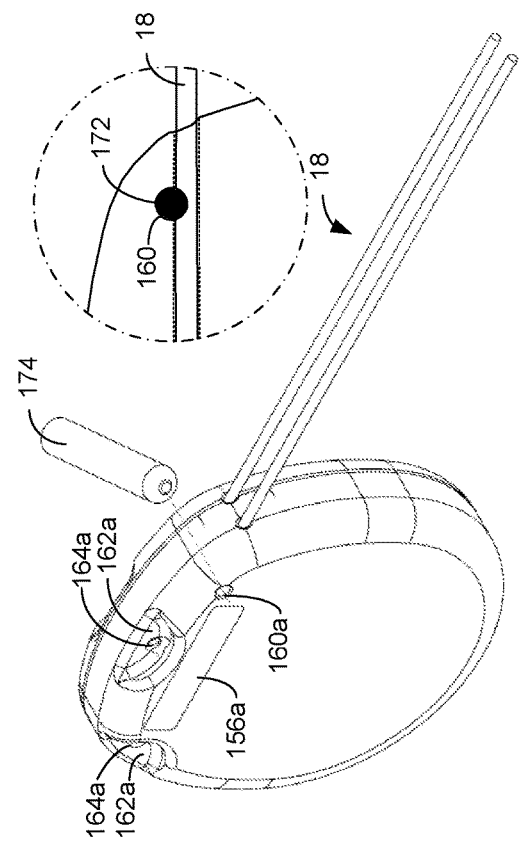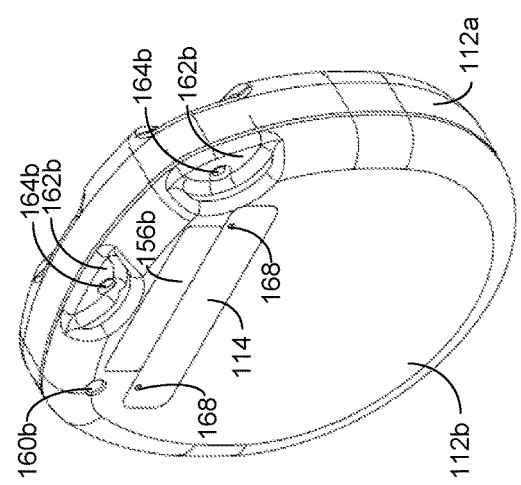
Figure 13
Figure 14
Figure 15

IMPLANTABLE MEDICAL DEVICE WITH A SILICONE HOUSING

CROSS-REFERENCE TO RELATED APPLICATIONS

This is a non-provisional of U.S. Provisional Patent Application Ser. No. 62/464,865, filed Feb. 28, 2017, to which priority is claimed, and which is incorporated herein by reference in its entirety.

FIELD OF THE TECHNOLOGY

The present application relates to an implantable medical device with a non-metallic housing. More specifically, the present application relates to an implantable medical device having a silicone housing and a silicone gel-filled interior.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the disclosed aspects within a Spinal Cord Stimulation (SCS) system, such as that disclosed in U.S. Pat. No. 6,516,227. However, the present disclosure may find applicability with any Implantable Medical Device (IMD) or in any IMD system.

As shown in FIG. 1, a traditional SCS system includes an IMD 10 (an Implantable Pulse Generator (IPG), more specifically), which includes a biocompatible device case 12 that is formed from a metallic material such as titanium. The case 12 typically comprises two components that are welded together, and it holds the circuitry and battery 14 (FIG. 2) necessary for the IPG 10 to function, which battery 14 may be either rechargeable or primary (non-rechargeable) in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make electrical contact with the electrode terminals 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary. In a traditional SCS application, two electrode leads 18 are typically implanted on the right and left side of the dura within the patient's spinal column.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-held, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

BRIEF DESCRIPTION OF THE DRAWINGS

FIG. 4 shows an isometric view of an electronic subassembly and an RF diverting assembly of the improved IMD in accordance with an aspect of the disclosure.

FIGS. 5A-5C show interior, cross-sectional, and exterior views, respectively, of a right side housing of the improved IMD in accordance with an aspect of the disclosure.

FIGS. 6A-6C show exterior, cross-sectional, and interior views, respectively, of a left side housing of the improved IMD in accordance with an aspect of the disclosure.

FIG. 7 shows a magnified view of an integral contact receptacle in the right side housing of the improved IMD in accordance with an aspect of the disclosure.

FIG. 8A shows a cross-sectional view of the joined left and right housings of the improved IMD with the internal components of the IMD removed in accordance with an aspect of the disclosure.

FIG. 8B shows a cross-sectional view of the joined left and right housings of the improved IMD with the internal components of the IMD visible in accordance with an aspect of the disclosure.

FIG. 8C shows a magnified view of a portion of FIG. 8B in accordance with an aspect of the disclosure.

FIG. 13 shows an isometric view of the right side of the improved IMD's housing with a conductive plate installed and with an exterior cavity filled with a silicone material (after the pins are permanently joined to the connector contacts) in accordance with an aspect of the disclosure.

FIG. 14 shows an isometric view of the left side of the improved IMD's housing with an exterior cavity filled with a silicone material and with an electrode lead inserted in each of the IMD's lead ports in accordance with an aspect of the disclosure. FIG. 14 additionally shows a lead latching tool, which includes a lead latching pin that is insertable into a lead latching hole of the improved IMD to maintain the position of the inserted electrode lead in accordance with an aspect of the disclosure.

FIG. 15 shows an isometric view of the improved IMD with the handle of the lead latching tool separated from the lead latching pin in accordance with an aspect of the disclosure. The lead latching pin is positioned in the IMD's lead latching hole to maintain the position of the inserted electrode leads in accordance with an aspect of the disclosure.

DETAILED DESCRIPTION

Figure 1:
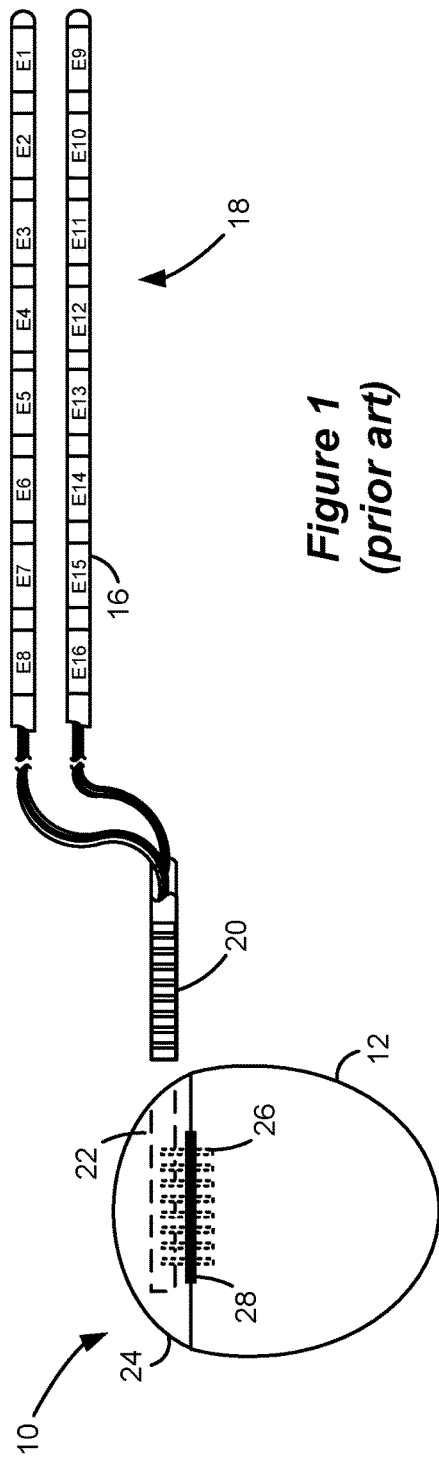
FIG. 1 shows an implantable pulse generator (IPG), in accordance with the prior art.
Figure 2:
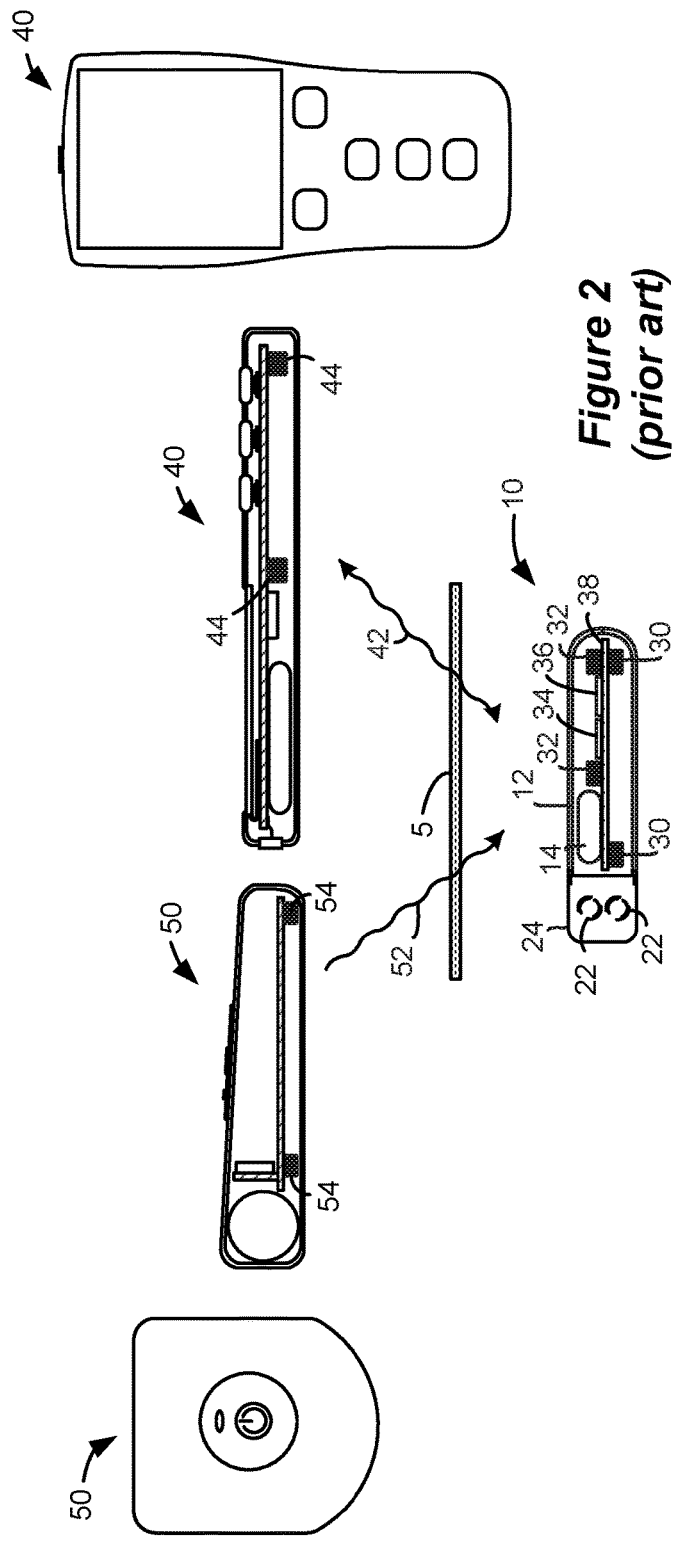
FIG. 2 shows a cross section of the IPG of FIG. 1 as implanted in a patient, as well as external devices that support the IPG, including an external charger and external controller, in accordance with the prior art.

The inventor has observed a number of drawbacks in traditional IMDs such as IMD 10. The IMD 10 includes a number of relatively expensive components such as the metallic case 12, the feedthrough 28, and the connector blocks 22. The hollow interior of the case 12 also necessitates the use of internal support structures to support the internal components such as the battery 14 and the PCB 38. In addition, the manufacturing of the IMD 10 is relatively labor intensive. For example, the case halves must be welded together to form the case 12, the hermetic feedthrough 28 must be secured to the case 12, the feedthrough pins 26 must be hermetically sealed at the feedthrough, the connector blocks 22 must be formed in the header 24, and the header 24 must be affixed to the case 12.

The metal case 12 also creates a number of problems. When the charger 50 is used to recharge the battery 14, the magnetic charging field 52 generates eddy currents in the metal case 12. The eddy currents reduce the charging rate (thus increasing the charging time) and generate heat that can potentially damage the patient's tissue and/or require the charger 50 to be operated at a reduced charging rate or to be deactivated for certain periods to allow the temperature to decrease (further increasing charging time). Eddy currents may also be generated in the metal case 12 as a result of the magnetic fields associated with magnetic resonance imaging (MRI). The eddy currents generated as a result of MRI fields generate heat and can create a torque that attempts to align the magnetic moment generated by the eddy currents with the MRI static field. This torque can produce differential forces that cause vibration between the internal components of the IMD and/or its case 12. Such vibration can cause cyclical fatigue failures, interfere with operation of the IMD 10, and even damage the patient's tissue. As a result, patients with traditional IMDs such as IMD 10 are often advised not to undergo MRI.

Figure 3:
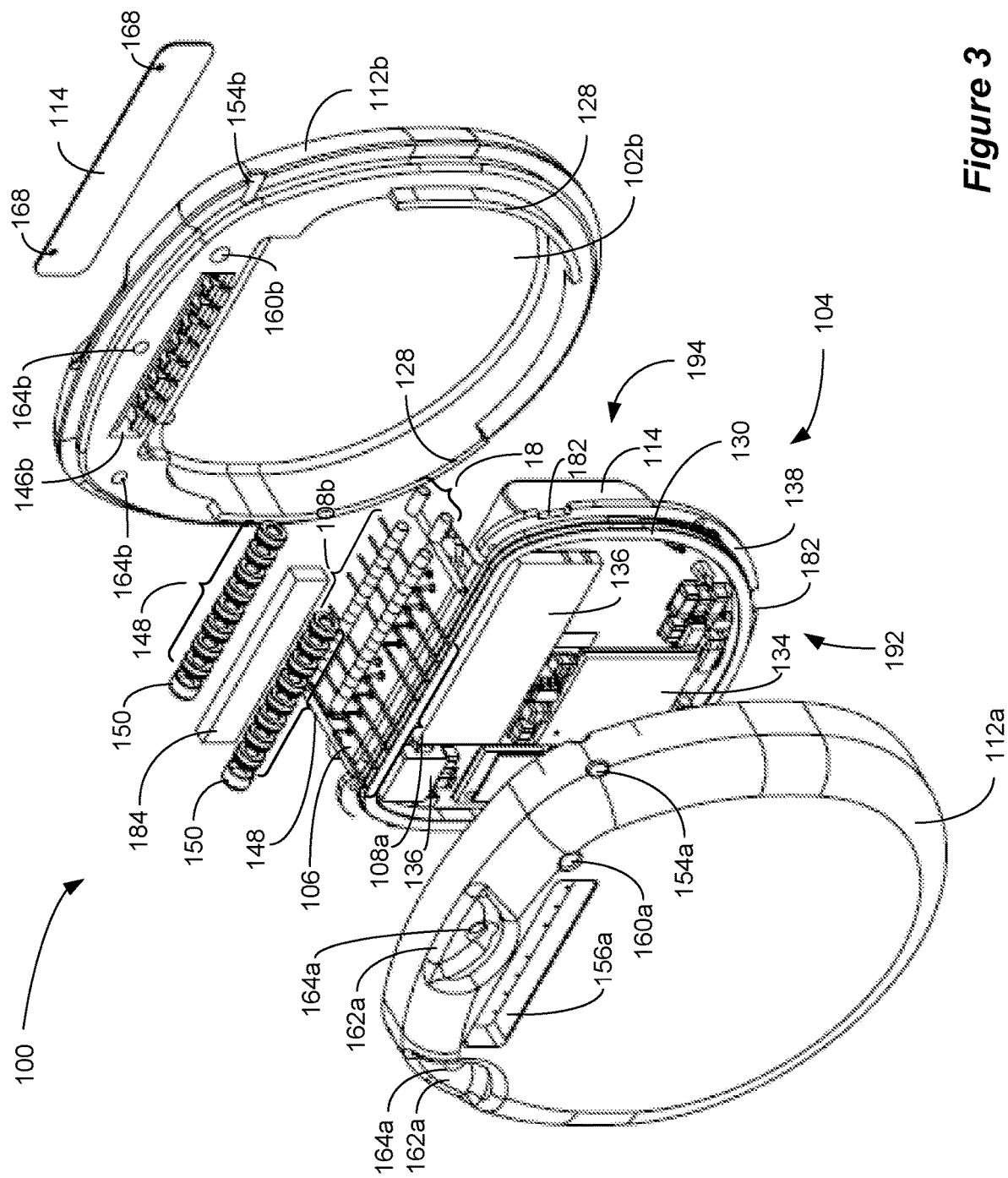
FIG. 3 shows an exploded isometric view of an improved implantable medical device (IMD) in accordance with an aspect of the disclosure.

FIG. 3 is an exploded view showing the various components of an improved IMD 100. The housing 112 of the improved IMD 100 is formed from a left housing 112a and a right housing 112b that are affixed to one another. The housings 112a and 112b are formed from a biocompatible polymer. In one embodiment, the biocompatible polymer is a hard, platinum cure silicone (e.g., a silicone rubber) such as NuSil Technology's MED-4780 or MED-4874 or a similar silicone material. Such silicone materials are generally hydrophobic and therefore prevent the ingress of fluids into the housing 112 when the IMD 100 is implanted in a patient. In a preferred embodiment, the housings 112a and 112b have a durometer of 80-90 Shore A, although softer or harder materials may also be used. The walls of the left and right housings 112a and 112b may have a thickness between two and three millimeters, although the thickness may be increased or decreased from this range depending on the material.

The case 112's silicone material is substantially less expensive than the metallic material from which the case 12 of the traditional IMD 10 is formed, and its use simplifies the assembly of the IMD 100 as compared to assembly of the IMD 10. Moreover, the silicone material enables the case 112 to be molded in a way that allows certain components of the traditional IMD 10 to be eliminated as described below.

The housings 112a and 112b, when joined, form a main interior cavity 102 within which an electronic subassembly 104 and an RF diverting assembly 106 are positioned. The electronic subassembly 104 includes a printed circuit board (PCB) 138 upon which a number of electrical components are integrated. Such components include a battery 114, a telemetry coil 132, a charging coil 130, a microcontroller 134, one or more ASICs 136, and a number of independent electrical components (not labeled). The microcontroller 134 provides general operational control of the IMD 100, and the one or more ASICs 136 include IMD-specific circuitry such as current generation circuitry that generates a current at each of a number of electrode nodes (each electrode node is ultimately connected to a corresponding electrode 16) in accordance with desired stimulation parameters (e.g., amplitude, polarity, pulse width, frequency, etc.). The one or more ASICs 136 additionally include circuitry to provide other IMD-specific functionality such as the functionality described above with respect to IPG 10. Additional details regarding the operation of the functional circuitry of an IMD are provided in U.S. Patent Publication No. 2012/0095529.

The RF diverting assembly 106 includes inductive elements that are positioned along the conductive paths from the current generation circuitry's electrode nodes on the PCB 138 to the electrodes 16 and/or capacitive elements that are positioned between the conductive paths and ground. The RF diverting assembly 106's inductive and/or capacitive elements are designed to impede and shunt to ground any currents that may be induced along the conductive paths, such as current induced when the IMD 100 is exposed to radio frequency (RF) irradiation associated with magnetic resonance imaging (MRI). The inductive elements in the current paths are sized to impede the flow of induced current at the comparatively high frequencies associated with MRI RF irradiation (e.g., 64 to 128 MHz), while having little or no effect on the comparatively low operational frequencies at which stimulation is performed. Likewise, the capacitive elements are sized to present a low impedance path to ground at the high frequencies associated with MRI RF irradiation, while presenting a high impedance path to ground at the lower operational frequencies of the stimulation system. The RF diverting assembly 106 protects the patient's tissue and the IMD 100's electrical circuitry from currents induced as a result of exposure to MRI RF irradiation. Additional details regarding the RF diverting assembly can be found in U.S. Pat. No. 9,084,380, which is incorporated herein by reference in its entirety.

FIG. 4 shows the electronic subassembly 104 connected to the RF diverting assembly 106 by a flex circuit 126. In one embodiment, the RF diverting assembly 106's inductive elements may be formed on the flex circuit 126 (in which case the flex circuit 126 would form part of the RF diverting assembly 106). The flex circuit 126 includes a number of conductive traces that are each connected to an electrode node on the PCB 138 at one end and to one of the pins 108a/b at the other end. The conductive traces on the flex circuit 126 and the pins 108a/b form a portion of the conductive path between the current generation circuitry and the electrodes 16. In the illustrated embodiment, there are 16 pins 108a/b, which correspond to the 16 electrodes 16. Half of the pins 108a (eight in the illustrated embodiment) are bent in the direction of the first side 192 of the PCB 138 and the other half of the pins 108b are bent in the direction of the second side 194 of the PCB 138. As noted above, the number of electrodes 16 (and therefore the number of pins 108a/b) is design specific and therefore may vary. In one embodiment, a coating that includes parylene and an inorganic component such as silicon nitride, silicone dioxide, or silicone oxinitride may be applied to the electronic subassembly 104 and the RF diverting assembly 106 (with the exception of at least the distal ends of the pins 108) as described in U.S. Pat. No. 7,742,817.

FIGS. 5A-5C provide interior, cross-sectional, and exterior views of the right housing 112b. The interior of the right housing 112b includes a main cavity 102b, which forms a portion of the main cavity 102 within which the electronic subassembly 104 and the RF diverting assembly 106 are positioned. Two PCB projections 128 are positioned just outside of the perimeter of the main cavity 102b. When the electronic subassembly 104 and the RF diverting assembly 106 are positioned within the main cavity 102, the PCB projections 128 contact the second side 194 of the PCB 138. The PCB projections 128 are spaced from the wall of the right housing 112b such that the battery 114 is positioned in close proximity to the wall (FIG. 8b) of the housing 112b. The cavity 102b includes two holes 140b that receive the RF diverting assembly's pins 142b (FIG. 4). As described below, the conductive pins 142b are welded on the exterior of the housing 112 to a conductive plate 114, which plate 114 acts as a current conduction terminal. The conductive pins 142b provide an electrical connection between the RF diverting assembly 106's capacitive elements and the conductive plate 114. When the RF diverting assembly 106 is positioned within the cavity 102b, the pins 108b extend through the small pin holes 144b (eight are shown in the illustrated embodiment) to the exterior of the right housing 112b.

Just above the cavity 102b in the interior of the housing 112b is an integral contact receptacle 146b that is designed to receive electrical contacts 148 (FIG. 3) and, ultimately, an electrode lead 18. In the illustrated embodiment, the receptacle 146b is configured to receive eight contacts 148 and one end stop 150 (FIG. 3). As illustrated in the magnified view in FIG. 7, the receptacle 146b is formed with a number of C-shaped frames 152b that each accommodate an individual contact 148 or end stop 150. Each frame 152b is sized such that insertion of a contact 148 or stop 150 into the frame 152b establishes an interference fit that maintains the position of the contact 148 or stop 150 within the receptacle 146b. When the contacts 148 are positioned within the frames 152b, they are axially aligned such that a lead 18 may be inserted into a lead port 154b and through the lead passage created by the holes in the center of the contacts 148. The frames 152b are spaced such that when the proximal end of the lead 18 is positioned against the end stop 150, each electrode terminal 20 on the lead 18 is aligned with a corresponding one of the contacts 148. This establishes an electrical connection between the contacts 148 and their associated electrodes 16 at the distal end of the lead 18.

Returning to FIG. 5C, the exterior of the right housing 112b includes a pin/connector cavity 156b (which corresponds to the receptacle 146b), a conductive plate cavity 158, a lead latching hole 160*b*, and two recesses 162*b* (each surrounding a suture hole 164*b* that penetrates through the housing 112*b*). The pin/connector cavity 156*b* includes several connector access windows 166*b* and the pin holes 144*b* (eight of each are shown, but more or fewer could also be utilized). The connector access windows 166*b* and the pin holes 144*b* extend through the wall of the housing, and the pin/connector cavity 158 facilitates electrical connection of the pins 108*b* with the connectors 148 from the exterior of the IMD 100 after the left and right housings 112*a* and 112*b* are joined as described below.

The conductive plate cavity 158 receives the conductive plate 114 (FIG. 3), which plate 114 is formed from a conductive biocompatible material such as titanium and which fits snugly within the cavity 158. In a traditional IMD 10, the case 12 can be utilized as an electrode. Because the housing 112 of the IMD 100 is nonmetallic and nonconductive, the conductive plate 114 takes the place of the traditional case 12 and can serve as a stimulation terminal (cathode or anode). The two holes 140*b* that receive the conductive pins 142*b* of the RF diverting assembly 106 extend through the housing 112*b* into the cavity 158. The holes 140*b* align with holes 168 in the plate 114 and enable the permanent connection of the conductive pins 142*b* to the conductive plate 114, which establishes the conductive path by which the RF diverting assembly 106 shunts induced currents to ground. The cavity 158 additionally includes two gel injection holes 170 that enable injection of a silicone gel into the interior cavity 102 of the IMD 100 after the left and right housings 112*a* and 112*b* are joined as described below.

FIGS. 6A-6C provide exterior, cross-sectional, and interior views of the left housing 112*a*. The exterior of the left housing 112*a* includes several features that mirror features in the right housing 112*b*'s exterior: a pin/connector cavity 156*a* with connector access windows 166*a* and pin holes 144*a*, a lead latching hole 160*a*, and two recesses 162*a* (each surrounding a suture hole 164*a* that penetrates through the housing 112*a*). The pin/connector cavity 156*a* functions in the same way as the corresponding feature of the right housing 112*b*. The lead latching hole 160*a* and the two recesses 162*a* and suture holes 164*a* are aligned with the corresponding components in the right housing 112*b*. The alignment of the lead latching holes 160*a/b* in the left and right housings 112*a/b* forms a lead latching hole 160 within which a lead latching pin 172 is inserted to maintain the position of leads 18 inserted into the lead port 154*a/b* as described below. The alignment of the receptacles 162*a/b*, and, more specifically, the suture holes 164*a/b* in the receptacles 162*a/b*, forms two suture holes 164 that enable the IMD 100 to be attached to a patient's tissue when the IMD 100 is implanted. Note that the exterior of the left housing 112*a* does not include a conductive plate cavity as does the exterior of the right housing 112*b*.

The interior of the left housing 112*a* includes a main cavity 102*a* that is aligned with the cavity 102*b* to form the main interior cavity 102 within which the electronic subassembly 104 and the RF diverting assembly 106 are positioned. The main cavity 102*a* includes a PCB stop 178 against which the first side 192 of the PCB 138 is positioned. When the PCB 138 is positioned against the PCB stop 178, several tabs 180 around the perimeter of the PCB stop 178 are aligned with notches 182 (FIG. 3) in the PCB 138. The PCB stop 178 is spaced from the wall of the housing 112*a* such that the electrical components mounted on the first side 192 of the PCB 138 are positioned in close proximity to the wall (FIG. 8B) of the left housing 112*a*. The interior of the left housing 112*a* additionally includes two holes 140*a* that receive the RF diverting assembly's pins 142*a*. Note, however, that the pins 142*a* are shorter than the pins 142*b* (FIG. 4) and that the holes 140*a* do not extend all the way through the left housing 112*a* as do the holes 140*b* through the right housing 112*b*. When the RF diverting assembly 106 is positioned within the cavity 102*a*, the pins 108*a* extend through the small pin holes 144*a*.

Referring to FIG. 6C, the interior of the left housing 112*a* includes a contact receptacle 146*a* that mirrors the contact receptacle 146*b*. The contacts 148 within the receptacle 146*a* are aligned with corresponding electrode terminals 20 on a lead 18 inserted within the lead port 154*a*. As illustrated in FIGS. 3, 8B, and 8C, the contacts 148 in the adjacent receptacles 146*a* and 146*b* are isolated from each other by an insulating spacer 184, which is formed of an electrically insulating material such as polyether ether ketone (PEEK) or polycarbonate.

With the internal components of the IMD 100 properly positioned (i.e., the contacts 148, RF diverting assembly 106, and electronic subassembly 104), the left and right housings 112*a* and 112*b* are joined. FIG. 8A provides a cross-sectional view of the joined housings 112*a* and 112*b* taken along the lines B-B of FIG. 5C with the internal components of the IMD 100 removed. FIG. 8B provides a similar cross-sectional view of the joined housings 112*a* and 112*b* taken along the lines A-A of FIG. 6A with the internal components visible. FIG. 8C provides a magnified view of the identified portion of FIG. 8B.

The left and right housings 112*a* and 112*b* are joined by applying an adhesive around the edges of the housings 112*a* and 112*b*. In one embodiment, the left and right housings 112*a* and 112*b* are joined by applying a bonding silicone primer such as Nusil Technology's SP-112, SP-270, MED-163 or a similar silicone primer and a silicone adhesive such as Nusil Technology's MED2-4213, MED3-4213, MED1-4013 or a similar silicone adhesive. In particular, the silicone primer and silicone adhesive are applied along a lip 186 in the left housing 112*a* and along a channel 188 in the right housing 112*b*. The left and right housings 112*a* and 112*b* are then joined together with the lip 186 positioned in the channel 188, which maintains the positions of the housings 112*a* and 112*b* while the adhesive cures. When the housings 112*a* and 112*b* are joined, the PCB protrusions 128 along the perimeter of the interior cavity 102*b* of the housing 112*b* are positioned against the second side 194 of the PCB 138 such that the PCB 138 is clamped between the PCB stop 178 and the PCB protrusions 128. The alignment of the tabs 180 within the PCB 138's notches 182 and the position of the PCB 138 between the PCB stop 178 and the PCB protrusions 128 ensures that the PCB 138's position is fixed within the interior cavity 102 of the housing 112. FIG. 8C illustrates the lead passages formed by the center holes of the aligned contacts 148 in the receptacles 146*a/b*. As described above, when the proximal end of a lead 18 is inserted into the lead port 154*a/b* and along the lead passage through the contacts 148, the contacts 148 are electrically coupled to corresponding electrode terminals 20 on the proximal end of the lead 18, which electrode terminals 20 are ultimately coupled to the electrodes 16 on the distal end of each lead.

Figure 10B:
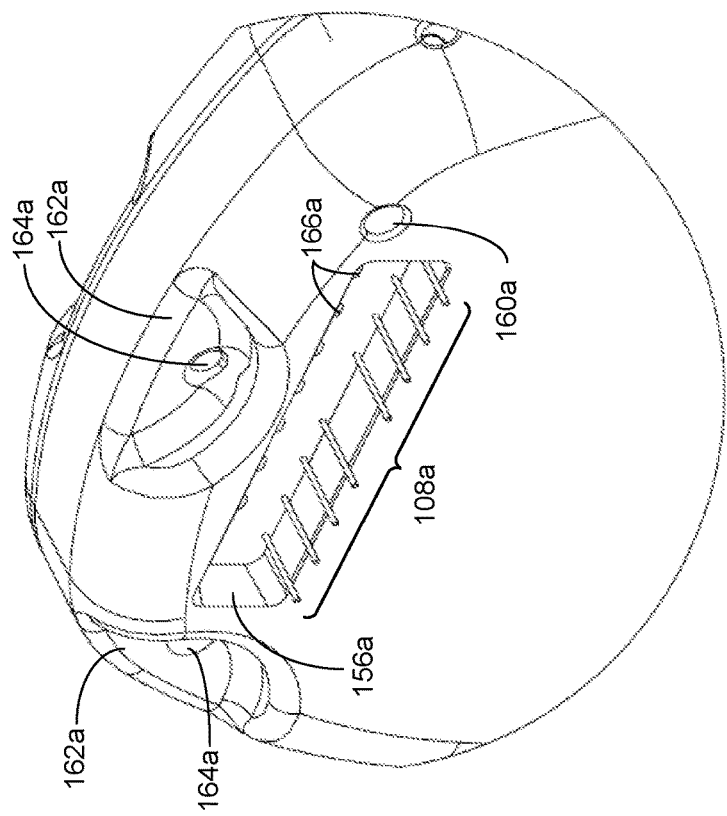
FIG. 10B shows a magnified view of a portion of FIG. 10A in accordance with an aspect of the disclosure.
Figure 9:
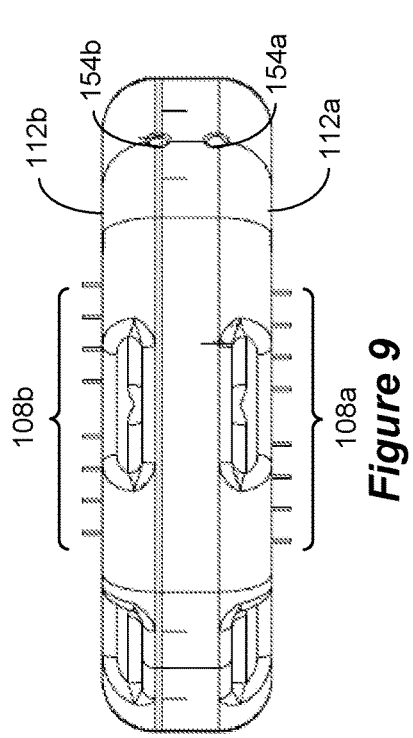
FIG. 9 shows a top view of the improved IMD with pins extending from the IMD's housing prior to the connection of the pins to contacts positioned in the housing in accordance with an aspect of the disclosure.
Figure 10A:
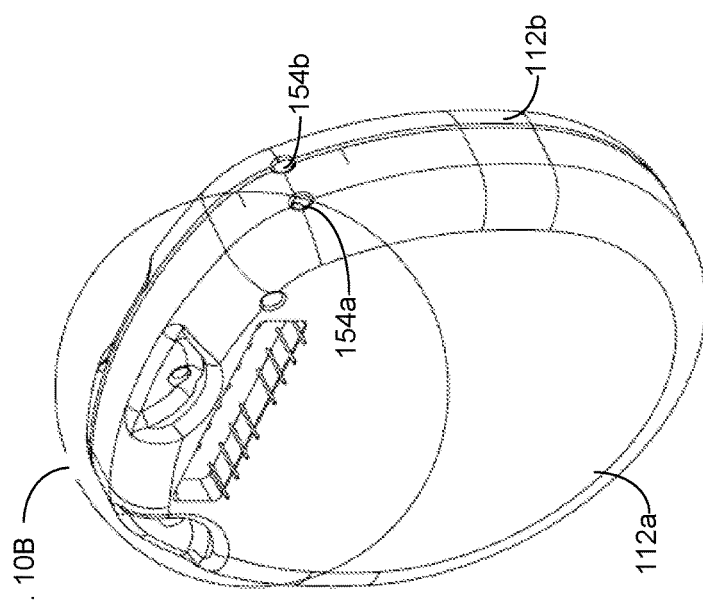
FIG. 10A shows an isometric view of the improved IMD with pins extending from the IMD's housing prior to the connection of the pins to contacts positioned in the housing in accordance with an aspect of the disclosure.
Figure 12B:
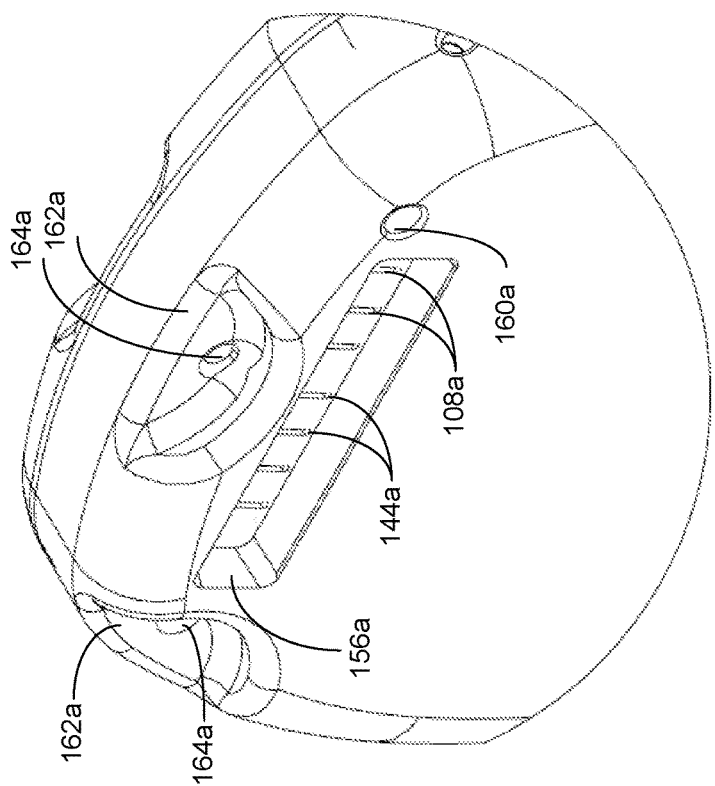
FIG. 12B shows a magnified view of a portion of FIG. 12A in accordance with an aspect of the disclosure.
Figure 11:
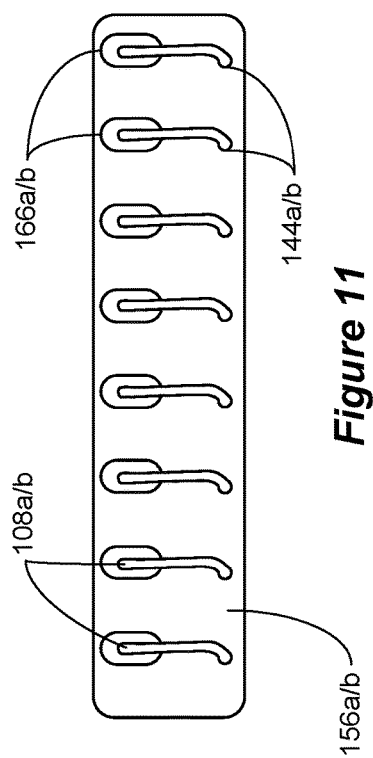
FIG. 11 shows an exterior cavity of the improved IMD with pins bent and permanently joined to lead connector contacts within the IMD's housing through contact windows in accordance with an aspect of the disclosure.
Figure 12A:
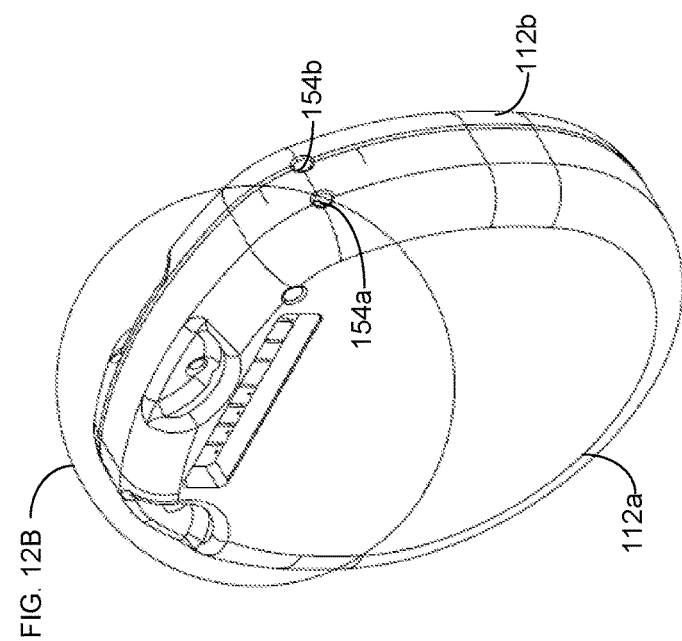
FIG. 12A shows an isometric view of the improved IMD with pins bent and permanently joined to connector contacts within the IMD's housing in accordance with an aspect of the disclosure.

As illustrated in FIGS. 9, 10A, and 10B, when the housings 112*a* and 112*b* are initially joined, the pins 108*a/b* extend outward from the body of the housing 112 through the holes 144*a/b*. Each pin 108 is then bent upward such that it comes into contact with its corresponding contact 148, which is accessible through a window 166 as illustrated in FIGS. 11, 12A, and 12B. After the pins 108*a/b* are bent into position, each pin 108 is welded (e.g., laser welded) to its corresponding contact 148 to maintain the electrical connection between the pin 108 and the contact 148. As described above, each pin 108 is ultimately electrically connected to an electrode node in the current generation circuitry. Therefore, connection of the pins 108a/b to the contacts 148 provides an electrical connection between the current generation circuitry and the electrodes 16 when an electrode lead 18 is subsequently positioned in the lead port 154a/b.

After the pins 108a/b have been welded to the contacts 148, the conductive plate 114 is installed, the pin/connector cavities 156a/b are filled with a silicone material, and the interior of the housing 112 is filled with a filler such as a silicone gel. If the holes 170 are used to fill the interior of the housing 112 with gel, then the gel must be injected prior to installation of the conductive plate 114, which blocks the holes 170. If, however, the lead ports 154a/b are used to inject the gel, then the gel can be injected as the final step after the conductive plate 114 is installed and the exterior cavities 156a/b are filled with silicone. In any event, these activities are described below without any implied order of performance.

The conductive plate 114 is secured in the cavity 158 using a silicone primer and adhesive such as those used to join the left and right housings 112a and 112b. The pins 142b extend through the holes 168 in the conductive plate 114, and they are welded to the conductive plate 114 (on the exterior side of the plate 114) to maintain the electrical connection between the pins 142b and the plate 114.

The cavities 156a/b are filled with silicone (e.g., a silicone rubber), which may be the same material from which the housing 112 is formed and which is applied directly over the bent and welded pins 108a/b. The silicone in the cavities 156a/b may be cured at ambient temperature, or at increased temperature, and it may also be subjected to a post-curing process.

The interior of the housing 112 is filled with a silicone gel. The silicone gel is injected slowly into either a hole 170 or a lead port 154a/b (or both) to completely fill the voids in the interior of the housing 112. The gel injection process may be performed in a vacuum environment. The silicone gel platinum cures to a soft, high penetration silicone. Examples of suitable silicone gels include a diphenyl cross-linked gel having very low Water Vapor Transmission Rate (WVTR) and Oxygen Transmission Rate (OTR) such as NuSil Technology's GEL-8250P or LS-3445 or other low WVTR gel. The low WVTR and OTR silicone gel, having hydrophobic properties, prevents ingress of bodily fluids and vapor into the housing when the IMD 100 is implanted. The silicone gel additionally acts as a thermal and electrical insulator and dampens mechanical vibrations that may be induced, for example, when the IMD 100 is exposed to RF irradiation associated with an MRI.

In one embodiment, the silicone gel is injected slowly into one of the lead ports 154a/b. The injected gel flows through one or more channels 190a/b (FIG. 7) that extend from the contact receptacle 146a/b to the main cavity 102 (e.g., between the frames 152a/b). As the main cavity 102 fills, the silicone gel will begin to fill the voids in the receptacles 146a/b, which insulates the contacts 148 from each other. Because the gel insulates the contacts 148, separate insulators that are utilized in traditional lead connector assemblies are not needed in the IMD 100. The interior of the housing 112 is completely filled when gel begins to flow out of the lead port 154a/b other than the port 154a/b that is used to inject the gel.

The silicone gel can also be injected into one of the holes 170 using a similar process. As illustrated in FIG. 5A, the holes 170 are located inside the main cavity 102b of the right housing 112b. So, in one embodiment, the holes 170 may be utilized to fill the main cavity 102 with silicone gel and the lead ports 154a/b may be utilized to fill the voids above the main cavity 102 with silicone gel. After the silicone gel has cured, plugs may be inserted into the lead ports 154a/b although this is not strictly necessary as the gel itself acts to prevent the ingress of any contaminants.

FIGS. 13 and 14 illustrate the IMD 100 with the plate 114 adhered to the housing, the pins 142b welded to the plate 114, and the cavities 156a/b filled with silicone. Although the gel cures to a firm consistency, it is penetrable such that the leads 18 can eventually be easily inserted into the lead ports 154a/b (e.g., when the IMD 100 is implanted) as illustrated in FIG. 14. The leads 18 are maintained in their position by a latching pin 172 that is inserted in the lead latching hole 160. The latching pin 172 is carried at the end of a handle 174 of a latching pin tool 176. With the leads 18 properly positioned in the lead ports 154a/b, the latching pin 172 is inserted into the lead latching hole 160 and the handle 174 is separated from the pin 172, leaving the pin 172 in the hole 160. As illustrated in FIG. 15, the latching pin 172 pinches the leads 18, preventing the leads 18 from being withdrawn. Additional details regarding the use of a latching pin for securing leads in a lead connector can be found in U.S. Provisional Patent Application No. 62/464,710, which was filed on Feb. 28, 2017, and which is incorporated herein by reference in its entirety.

The IMD 100 overcomes several problems associated with traditional IMDs 10. The IMD 100's silicone housing 112 is a significantly less expensive material than the IMD 10's titanium housing 12. In addition, the silicone housing 112 greatly reduces the labor costs associated with assembling the IMD 100 as compared to the IMD 10. As described above, the left and right housings 112a and 112b are adhered together, which is significantly less labor-intensive than welding the two halves of the case 12 around a feedthrough assembly 28 and subsequently affixing the separate header 24 to the case 12 as required in the construction of the traditional IMD 10. In addition, the silicone material of the housing 112 is molded in a way that allows certain components of the IMD 10, such as the separate header 24 and connector assemblies 22, the hermetic feedthrough 28, and various internal support structures, to be eliminated. All of this leads to a lower cost of construction of the IMD 100 as compared to the IMD 10.

In addition, the silicone housing 112 does not attenuate the magnetic fields 42 and 52 used to communicate with the IMD 100 and charge its battery 114, thus enabling communications and charging over greater distances. Because the IMD 100 can be charged over greater distances, charging can be more easily incorporated into the patient's daily routine (i.e., chargers incorporated into furniture, clothing, etc.), which allows the IMD 100's battery 114 to be decreased in size. The silicone housing 112, being non-conductive, also eliminates the eddy currents (and the associated heating and vibration concerns) that are generated in the IMD 10's metallic case 12 as a result of the communication 42, charging 52, or MRI magnetic fields. Moreover, the effects of any heating or vibration associated with the generation of eddy currents in conductive components within the IMD 100 are minimized as a result of the thermal and mechanical insulative properties of the silicone gel in the interior of the housing 112. Thus, the IMD 100 is much more cost efficient to construct and overcomes a number of technical problems associated with traditional IMDs 10.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. An implantable medical device (IMD), comprising:
   a silicone housing having an interior cavity and at least one integral interior contact receptacle;
   an electronic subassembly that is positioned within the interior cavity; and
   a plurality of contacts that are positioned within the at least one interior contact receptacle, wherein:
   each of the plurality of contacts comprises a hole, wherein the at least one integral interior contact receptacle comprises a plurality of frames integrated into the silicon housing, each configured to accommodate one of the plurality of contacts such that the plurality of frames maintains the plurality of contacts in an axial alignment so that the holes form a lead passage configured to accept a lead.

2. The device of claim 1, further comprising at least one electrode lead port that corresponds to the at least one interior contact receptacle.

3. The device of claim 2, wherein each interior contact receptacle is configured to receive a proximal end of an electrode lead inserted into its corresponding lead port.

4. The device of claim 1, wherein the electronic subassembly comprises current generation circuitry that is configured to generate a current at each of a plurality of electrode nodes, wherein each one of the electrode nodes is electrically connected to a corresponding one of the contacts.

5. The device of claim 4, further comprising at least one exterior cavity that corresponds to the at least one interior contact receptacle.

6. The device of claim 5, wherein the at least one exterior cavity comprises a plurality of windows and a plurality of pin holes that extend through the housing.

7. The device of claim 6, wherein each of the plurality of contacts is accessible from the exterior cavity through one of the plurality of windows.

8. The device of claim 6, wherein the electrical connection between each electrode node and its corresponding contact comprises a pin that extends through one of the plurality of pin holes.

9. The device of claim 8, wherein each pin is welded to one of the plurality of contacts through one of the windows.

10. The device of claim 9, wherein the at least one exterior cavity is filled with a silicone material.

11. The device of claim 4, further comprising an RF diverting assembly that is positioned in the interior cavity.

12. The device of claim 11, wherein the RF diverting assembly comprises a plurality of capacitive elements, wherein each capacitive element is coupled between the electrical connection between one of the electrode nodes and its corresponding contact and a conductive plate that is attached to the exterior of the housing.

13. The device of claim 12, wherein the RF diverting assembly further comprises a plurality of inductive elements, wherein each inductive element is connected between one of the electrode nodes and its corresponding contact.

14. The device of claim 1, further comprising a conductive plate that is positioned in a conductive plate cavity in the exterior of the housing.

15. The device of claim 1, wherein the at least one interior contact receptacle comprises a silicone gel configured to insulate each of the plurality of contacts from each other.

16. The device of claim 15, wherein the silicone gel is a diphenyl cross-linked silicone gel.

17. The device of claim 1, wherein the housing comprises a first housing and a second housing that are joined together with an adhesive.

18. The device of claim 17, wherein the first housing comprises a lip that is positioned within a corresponding channel in the second housing.

19. The device of claim 17, wherein the at least one interior contact receptacle comprises a first interior contact receptacle in the first housing and a second interior contact receptacle in the second housing.

* * * * *